(12) United States Patent
Babich et al.

(10) Patent No.: US 6,437,103 B1
(45) Date of Patent: Aug. 20, 2002

(54) FATTY ACID ANALOGS FOR DIAGNOSIS OF CORONARY ARTERY DISEASE

(75) Inventors: John W. Babich, Scituate; Kevin Maresca, Tewksbury; Timothy Shoup, Waltham; David R. Elmaleh, Newton, all of MA (US)

(73) Assignee: Biostream Inc., Cambridge, MA (US)

( * ) Notice: Subject to any disclaimer, the term of this patent is extended or adjusted under 35 U.S.C. 154(b) by 0 days.

(21) Appl. No.: 09/549,732

(22) Filed: Apr. 14, 2000

Related U.S. Application Data

(60) Provisional application No. 60/129,298, filed on Apr. 14, 1999.

(51) Int. Cl.$^7$ ............................................. C07F 13/00
(52) U.S. Cl. ............................... 534/14; 556/1; 556/45
(58) Field of Search .............................. 534/14; 556/45, 556/1

(56) References Cited

U.S. PATENT DOCUMENTS

| | | | |
|---|---|---|---|
| 4,524,059 A | 6/1985 | Elmaleh et al. | 424/1.1 |
| 4,615,876 A | 10/1986 | Troutner et al. | 424/1.1 |
| 4,746,505 A | 5/1988 | Jones et al. | 424/1.1 |

FOREIGN PATENT DOCUMENTS

| | | |
|---|---|---|
| WO | wo 97/19705 | 5/1997 |

OTHER PUBLICATIONS

Yamamura, Norio et al. "Technetium–99m–Labeled Medium–Chain Fatty Acid Analogues Metabolized by β–Oxidation: Radiopharmaceutical for Assessing Liver Function" *Bioconjugate Chemical*, vol. 10, pp. 489–495 (1999).

Atsma, D.E., et al. "Potential of $^{99M}$Tc–LDLs Labeled by Two Different Methods for Scintigraphic Detection of Experimental Atherosclerosis in Rabbits" *Arteriosclerosis and Thrombosis*, vol. 13, No. 1, pp. 78–83, Jan. 1993.

Okada, Robert D., "Tellurium–Labeled Fatty–Acid Analogs: Relationship of Heteroatom Position to Myocardial Kinetics" *European Journal of Nuclear Medicine*, vol. 11, pp. 156–161 (1985).

Elmaleh, David R, et al. "Myocardial Imaging with 9–[Te–123m]Telluraheptadecanoic Acid" *The Journal of Nuclear Medicine*, vol. 22, No. 11, pp. 994–999 (1981).

Jones, Jr., G.S., et al. "7,10–BIS(2–Mercapto–2–Methyl)Propyl–7,10–Diazapalmitic Acid: A Novel, $N_2S_2$ Ligand For Technetium–99m" *Bioorganic & Medicinal Letters*, vol. 6, No. 20, pp. 2399–2404 (1996).

Alberto et al.; "A Novel Organometallic Aqua Complex of Technetium for the Labeling of Biomolecules: Synthesis of [$^{99m}$Tc(OH$_2$)$_3$(CO)$_3$]$^+$ from [$^{99m}$Tc O$_4$] in Aqueous Solution and Its Reaction with a Bifunctional Ligand", J. Am. Chem. Soc. 120: 7987–7988, (1998).

Alberto et al.; "Application of Technetium and Rhenium Carbonyl Chemistry to Nuclear Medicine. Preparation of [NE t 4]2 [Tc C13 (CO)3] FROM [NB u 4][TcO4]and Structure of [NE t4]Tc 2 (μ–C1 ) 3 (CO) 6]; Structure of the Model Complexes [NE t4][Re 2 (μ–OE t )2(μ–OAc)(CO) 6 ]and [ReBr ({–CH2 S (CH 2)2 C1 }2) (co)3]", Transition Met. Chem., 22: 597–601 (1997).

Alberto et al.; "First Application of Fac–[99m T c(OH2 )3 (CO)3]$^+$ in Bioorganometallic Chemistry: Design, Structure, and in Vitro Affinity of a 5–HT 1 A Receptor Ligand Labeled with 99mTc", J. Am. Chem. Soc. 121: 6076–6077, (1999).

Bassingthwaighte and Holloway, Jr.; "Estimation of Blood Flow with Radioactive Tracers", Seminars in Nuclear Medicine 6(2): 141–161, (Apr. 1976).

Bianco et al.; "Accumulation of Radioiodinated 15–(p–Iodophenyl)–6–Tellurapentadecanoic Acid in Ischemic Myocardium During Acute Coronary Occlusion and Reperfusion", JACC, 4(1): 80–87, (Jul. 1984).

Corbin et Work; "1 Alkyl–(or aryl–) amino–2–methylpropane–2–thiols. Some Bi–and Tetradente Nitrogen–Sulfur Ligands From Schiff's Base Disulfides", J. Org. Chem. 41(3):489–491, (1976).

Davidson et al.; "Fatty Acid Derivatives ω–Substituted With a Neural Technetium Complex", The Journal of Nuclear Medicine, p4, (Jun. 2, 1985).

Davidson et al.; "A New Class of Oxotechnetium (5+) Chelate Complexes Containing a Tc ON,s2 Core", America Chemical Society, 20(6): 1629–1632, (Jun. 1981).

Eckelman et al.; "New Compounds: Fatty Acid and Long Chain Hydrocarbon Derivatives Containing a Strong Chelatin Agent", Journal of Pharmaceutical Science, 64(4): 704–706, (Apr. 1975).

Elmaleh et al.; "Myocardial Imaging With 9–[Te–123m] Teluraheptadecanoic Acid", The Journal of Nuclear Medicine, 22(11):994–999, (1981).

Gateley et al.; "On the Rate–Limiting Step In Myocardial Clearance of Label from 16—Iodohexadecanoic Acid (IHDA)", J. Nucl. Med. 24: Pl2, (1983) (Abstract).

Goldfarb et al.; "Comparison of Tc–99m Aminoethyl Diaminodithiol", J. Nucl. Med. 27: 1050, (1986).

Goldstein et al.; "External Assessment of Myocardial Metabolism with C–11 Palmitate In Vivo", J. Nucl. Med. 21: 341–348, (1980).

Goodman et al,; "Synthesis and Evaluation of Radioiodinated Terminal p–Iodophenyl–Substituted α–and β–Methyl–Branched Fatty Acids", J. Med. Chem. 27: 390–397, (1984).

(List continued on next page.)

Primary Examiner—Porfirio Nazario-Gonzalez
(74) Attorney, Agent, or Firm—Foley, Hoag & Eliot, LLP

(57) ABSTRACT

Radioimaging agents, which exhibit high uptake and retention in the myocardium are disclosed.

24 Claims, No Drawings

OTHER PUBLICATIONS

Goodman et al.; "New Myocardial Imaging Agents: Synthesis of 15–(p–Iodophenyl)–3 (R,S)–Methylpentadecanoic Acid by Decomposition of a 3,3–(1,5–Pentanediyl) triazene Precursor", J. Org. Chem. 49:2322–2325, (1984).

Heymann et al.; "Blood Flow Measurements With Radionuclide–Labeled Particles", Progress in Cardiovascular Disease, XX (1): 55–79, (Jul./Aug. 1977).

Kuung et al.; "Tc–99 Complexes Based on $N_2S_2$ Ligands", H. Nucl. Med., 27: 1051, (1986), (Abstract).

Kung et al.; "Synthesis and Biodistribution of Neutral Lipid–Soluble Tc–99m Complexes that Cross the Bloob–Brain Barrier", The Journal of Nuclear Medicine, 25(3): 326–332, (1984).

Kung et al.; "Synthesis of New Bis(aminoethanethiol) (BAT) Derivatives: Possible Ligands for $^{99m}$Tc Brain Imaging Agents", J. Med. Chem. 28: 1280–1284, (1985).

Leirer et al.; "Electronic Spectra of 1, 2–diminetricarbonyl-rhenium (I)chloride complexes with Imidazole Derivatives as Ligands", Inorganica Chimica Acta, 288: 150–153, (1999).

Lerch et al.; "Effect of Flow–Independent Reduction of Metabolism on Regional Myocardial Clearance of 11 C–Palmitate", Circulation, 65(4):731–738, (Apr. 1982).

Lever et al.; "Design, Preparation, and Biodistribution of a Technetium–99m Triaminedithiol Complex to Assess Regional Cerebral Blood Flow", J. Nucl. Med. 26: 1287–1294, (1985).

Livni et al.; "Beta–methyl[1–11 C] heptadecanoic Acid: A New Myocardial Metabolic Tracer for Positron Emission Tomography", J. Nucl. Med. 23(2): 169–175, (1982).

Mchulla et al.; "Comparative Evaluation of Fatty Acids Labeled with C 11, cl–34M, Br–77, and |–123 for Metabolic Studies of the Myocardium: Concise Communication", The Journal of Nuclear Med. 19(3): 298–302, (1978).

Miller et al.: "Imaging Characteristics of a New Single–Photon Myocardial Metabolic Tracer", Circulation(Abstract) 74(Suppl. II): II–62(245), (Oct. 1986).

Miller et al.; "Modified Fatty Acid Analog Imaging: Correlation of SPECT and Clearance Kinetics in Ischemic–Reperfused Myocardium", J. Nucl. Med. 26: P88, (1985, Abstract).

Most et al.; "Free Fatty Acid Metabolism of the Human Heart at Rest", The Journal of Clinical Investigation, 48: 1177–1188, (1969).

Neely and Morgan.; "Relationship Between Carbohydrate and Lipid Metabolism and the Energy Balance of Heart Muscle", Annual Review of Physiol. 36: 413–459, (1974).

Neely and Oram,; "Myocardial Utilization of Carbohydrate and Lipids", Progress in Cardiovascular Disease, XV (3): 289–329, (Nov./Dec. 1972).

Poe et al.; "Myocardial Extraction of Labeled Long–Chain Fatty Acid Analogs", Proceedings of the Society for Experimental Biology and Medicine, 148: 215–218, (1975).

Reske et al.; "15(P–[$^{123}$]] Iodophenyl) Penadecanoic Acid as Tracer of Lipid Metabolism: comparison with [ 1–$^{14}$C] Palmitic Acid in Murine Tissues", J. Nucl. Med. 25(12): 1335–1342, ((1984).

Schelbert et al.; "C–I I Palmitate for the Noniinvasive Evaluation of Regional Myocardial Fatty Acid Metabolism with Positron computed Tomography.111. In Vivo Demonstration of the Effects of Substrate Availability on Myocardial Metabolism", Am. Heart J. 105: 492–504, (1983).

Schon et al.; "Measurement of Myocardial Fatty Acid Metabolism: Kinetics of Iodine–123 Heptadecanoic Acid in Normal Dog Hearts", J. Nucl. Med. 27(9):1449–1455, (Sep. 1986).

Schön et al.; "C–11 Labeled Palmitic Acid for the Noninvasive Evaluation of Regional Myocardial fatty Acid Metabolism With Positron–Computed Tomography I. Kinetics of C–11 Palmitic Acid in Normal Myocardium", Am. Heart J. 103: 532–561, (1982).

Sobel et al.; "Detection of Remote Myocardial Infarction in Patients With Positron emission Transaxial Tomography and Intravenous 11 C–Palmitate", Circulation 55: 851–853, (1997).

Warren et al.; "New Iodinated Phenyl Fatty Acids for Imaging Myocardial Metabolism", J. Nucl. Med. 27(6): 939–940, (Jun. 1986).

Weich et al.; "The Extraction of Thallium–201 by the Myocardium", Circulation, 56: 188–191, (1977).

Weiss et al.;"External Detection and Visualization of Myocardial Ischemia with 11 C–Substrates in Vitro and in Vivo", Circ. Res. 39(1): 24–32, (Jul. 1976).

Westera et al.; "A Comparison Between Terminally Radioiodinated Hexadecenoic Acid (*I–HA) and 201 T1–Thallium Chloride in the Dog Heart", J. Nucl. Med., 5: 339–343, (1980).

Whitmer et al.; "Control of Fatty Acid Metabolism in Ischemic and Hypoxic Hearts", The Journal of Biological Chemistry, 253(12): 4305–4309, (1978).

Ziergler L. Kenneth; "Fatty Acids as Substrate for Heart and Skeletal Muscle", Circ. Res. 38(6): 459–463, (Jun. 1976).

Bandoli et al.; "Structure of (Benzenethiolato)oxo [N–(2–sulfidophenyl)salicylidene–iminato(2–)–O,N,S] technetium(V)*", Acta Chrystallogr. Sect. C. 48: 1422–1425, (1992).

Clarke and Podbielski; "Medical Diagnostic Imaging with Complexes of $^{99m}$TC", Coordination Chemistry Reviews 78:253–331, (1987).

Fietz et al.; "Synthesis and Molecular Structure of Chloro (3–thiapentane–1,5–dithiolato)oxorhenium (V)", Inorganic Chimica Acta, 231:233–236, (1995).

Hom and Katzenellenbogen; "Technetium –99,–Labeled Receptor–Specific Small–Molecule Radiopharmaceuticals: Recent Developments and Encouraging Results", Nuclear Medicine & Biology, 24: 485–598, (1997).

Johannsen et al.; "Technetium(V) and Rhenium(V) Complexes for 5–HT 2A Serotonin Receptor Bibding: Structure–Affinity Considerations", Nucl. Med. And Biol. 23: 429–438, (1996(.

Maresca et al.; "Expansion of the '3+1' Concept of Oxorhenium–Thiolate Chemistry to Cationic and Binuclear Complexes", Inorganica Chemistry Communications 1: 209–212, (1998).

Maresca et al.; "Synthesis and Characterization of Oxorhenium–'3+1' Mixed–thiolate Complexes. Crystal and Molecular Structures of [ReO{η3 –(SCH 2 CH 2)2 S} (C6 H4 X–4–CH2S)](X= F, Cl, Br, Ome) and of the Pendant Thiolate Compounds [ReO {η3–(SCH2CH2)2 S} –(η 1 – SCH2CH2 SCH2CH2CH2CH2SH)] and [ReO {η3 –(sch2 ch2)2s}–{η1 –SCH2CH2CH(OH)CHCH(OH)CH2SH}]", Inorganica Chimica Acta, 284: 252–257, (1999).

Meegalla et al.; "Synthesis and Characterization of Technetium–99m–Labeled Tropanes as Dopamine Transporter–Imaging Agents", J. Med. Chem. 40: 9–17, (1997).

Nicholson et al.; "The Synthesis and Characterization of [MCl$_3$(N=NC$_5$H$_4$NH) (HN=NC$_5$H$_4$N)]from [MO$_4$]$^-$(where M=Re, Tc) Orgganodiazenido, Organozene–Chelate Complexes. The X–ray Structure of [ReCl$_3$ (N=NC$_5$H$_4$NH)(NH= NC$_5$H$_4$N)]" Inorganica Chimica Acta 252: 421–426, (1996).

Rose et al.; "Synthesis and Characterization of Organohydrazino Complexes of Technetium, Rhenium and Molybdenum with the {M($\eta^1$–Hx NNR) ($\eta^2$–Hy NNR)}Core and Their Relationship to Radiolabeled Organohydrazine-Derivatized Chemotactic Peptides with diagnostic Applications", Inorg. Chem. 37: 2701–2716, (1998).

Rose et al.; "Synthesis and Characterization of Rhenium Thiolate Complexes. Crystal and Molecular Structures of [NBu$_4$][ReO(H$_2$O)Br$_4$)]. 2H$_2$O, [Bu$_4$N][ReOBr$_4$ (OPPh$_3$)], [ReO(SC$_5$H$_4$N)$_3$], [ReO (SC$_4$H$_3$N$_2$)$_3$] [ReO(OH)(SC$_5$H$_4$N–3,6–(SiMe$_2$Bu$^t$)$_2$)$_2$], [Re(N$_2$COC$_6$H$_5$) (SC$_5$H$_4$N) Cl (PPh$_3$)$_2$)], and [Re (PPh$_{3)}$ (SC$_4$H$_3$N$_2$)$_3$]", Inorg. Chem. 35: 3548–3558, (1996).

Dudczak et al.; "The Usse of 123 I–labeled heptadecanoic Acid (HAD) as Metabolic Tracer: Preliminary Report", Europ. J. Nucl. Med. 9: 81–85, (1984).

Liefhold and Eisenhut;"Synthesis, Labeling, and Pharmacokinetics of 1 3 1 I Labeled Phenylene–Iophenyl–Fatty Acids (PHIPA)", Journal of Labeled Compounds and Radiopharmaceuticals, vol. XXIII (10–12): 1239–1241, (1986).

Livni et al.; "Synthesis and Biological Distribution of Tc–99m Labeled Palmitic Acid Derivatives", Radiopharmaceuticals II. Proceedings 2$^{nd}$ International Symposium on Radiopharmaceuticals, Mar. 19–22, pp. 487–495, (1979).

Livni et al.; "Radioiodinated β–Methyl Phenyl Fatty Acids as Potential Tracers For Myocardial Imaging and Metabolism", European Heart Journal, 6(Suppl. B): 85–89, (1985).

Mach et al.; "Synthesis and Biodistribution of Tc–99m BAT–PDA: A Potential Heart Imaging Agent for Spect", Journal of Labeled Compounds and Radiopharamceuticals vol. XXIII (10–12): 1138–1140, (1986).

FATTY ACID ANALOGS FOR DIAGNOSIS OF CORONARY ARTERY DISEASE

This application claims the benefit under 35 U.S.C. § 119(e) of U.S. Provisional Application No. 60/129,298, filed Apr. 14, 1999.

BACKGROUND OF THE INVENTION

Coronary artery disease (CAD) is the leading cause of death in the United States, accounting for roughly 24% of all deaths. The health care cost of cardiovascular diseases in 1999 is estimated by the AHA at $286.5 billion, a figure which includes direct costs, such as physicians, other professionals, hospital and nursing home services, the cost of medications, home health and lost productivity. Many of the deaths resulting from CAD may have been prevented if a valid, standardized technique existed which assessed the condition of the myocardium and allowed the use of appropriate therapy. Hence, there is a need for sensitive, reliable, and low cost techniques for early detection of heart disease and for monitoring the course of treatment.

Long-chain fatty acids are a major source of energy for the heart muscle and are rapidly metabolized by beta-oxidation under normal conditions. At rest and during exercise, non-esterified fatty acids supply approximately 65% of the energy requirement for myocardial metabolism while the remainder of myocardial energy needs are provided by glucose (15%), lactate and pyruvate (12%), and amino acids (5%) [Zieler et al. 1976, Neely et al. 1972, Opieet al. 1969, Mostet al. 1969]. Non-esterified fatty acids are taken up by the myocardium with an extraction of 40–60% and either transiently esterified to triglyceride or oxidized for energy [Schon et al. 1982, Poe et al. 1975, Machulla et al. 1978, Westera et al. 1980; Gately et al. 1983, Van der Wall et al. 1981]. In contrast, under conditions of reduced oxygen delivery to heart tissue such as ischemia and hypoxia, there is a dramatic decrease in fatty acid metabolism.

Fatty acid molecules have a unique structure and do not require carrier mediation for their transport. Fatty acids are bound to albumin and enter into the cell mainly by free diffusion through the capillary wall and sarcolemma into the intracellular space. This extraction is dependent mainly on the following parameters: the chain length of the fatty acid (double bonds and branching have secondary effects), the blood flow to the myocardium, the concentration of the fatty acid in plasma, and the metabolic state of the myocardial tissue. In addition, both lipophilic and carboxylic sides of the fatty acid molecule must be free of bonding in order to retain the transport and the biochemical properties of the molecule. Fatty acid interaction in the heart tissue is not of a receptor-ligand type. Therefore the rigidity of the fatty acid structure may not be the main determinant of their transport and biochemical degradation process.

Two compounds currently used in the U.S. and Europe for cardiac imaging are Tl-201 (DuPont/Mallinckrodt) and Cardiolite (DuPont). Both agents are useful and provide important information on myocardial function. However, these radiopharmaceuticals have certain important limitations. The main drawbacks are: (1) these agents are mainly flow tracers and do not directly address the metabolic viability of the injured myocurdium, and (2) image sensitivity is low for single vessel obstruction, however, it is improved with increased damage.

Many fatty acids or their analogs have been labeled with positron and gamma emitting radionuclides to non-invasively assess changes in fatty acid metabolism [Schon et al. 1982, Machulla et al. 1978, Lerch et al. 1982, Schon et al. 1986, Weiss et al. 1976, Sobel et al. 1977, Goldstein et al. 1980, Livni et al., 1982, Dudczak et al. 1984, Reske et al. 1984, Livni et al. 1985, U.S. Pat. No. 4,746,505]. These fatty acids have the radiolabel on the carboxylic carbon, in the middle, or on the terminal alkyl carbon. As a result, all of these agents are always subject to loss of the label during the degradation steps of the fatty acid beta-oxidation process.

A significant departure from the structure of a normal fatty acid, e.g. palmitate, or iodophenyl, did not result in a significant change in the fatty acid behavior of the compound. For example, 15-(p-iodophenyl)pentadecanoic acid [Goodman et al. 1984] and, even more notably, a series of phenyleneiodophenyl fatty acids [Liefhold and Eisenhut, 1986] all demonstrated moderate myocardial uptake. Members of the latter group differed in molecular weight from palmitate (mol. wt=256) by about 260 Dalton.

Although fatty acids labeled with positron emitting radionuclides in conjunction with tomographic techniques may be an excellent means of quantifying in vivo regional myocardial metabolism, they remain the exclusive research tool of a limited number of institutions. Iodine-123 labeled BMPPA showed promise in animal and human studies [Goodman et al. 1984, Miller et al. 1985], however, since $^{123}$I requires a cyclotron for production, it is unlikely that $^{123}$I-labeled fatty acids (uncontaminated with I-124) will become widely available for routine diagnostic use.

The excellent nuclear properties of Tc-99m and its widespread availability from a generator have made this radionuclide the most frequently used nuclide in nuclear medicine. Several groups over the past 20 years have attempted to develop a myocardial imaging agent in which a technetium chelating moiety was incorporated into a long chain fatty acid [Eckelman et al.1975, Livni et al. 1981, Davison et al 1985, Kelso et al. 1988, Cumming et al. 1988, Mach et al. 1986, 1988, 1989]. In all these cases, the radiolabeled fatty acids contained structural modifications wherein one side of the molecule, carboxyl or w-alkyl moiety, was chemically involved in the chelate moiety. As a result, these agents did not show heart uptake.

An agent that allows for noninvasive delineation of myocardial metabolism and which could be routinely prepared at most clinical institutions or purchased from a distribution center would be of considerable benefit in the diagnosis and treatment of heart disease. Myocardial energy demand is met primarily by fatty acid oxidation. Radiolabeled fatty acids that display efficient myocardial uptake and adequate myocardial retention are attractive candidates for clinical evaluation of regional discrepancies in fatty acid metabolism which occur in ischemic heart disease and cardiomyopathies.

SUMMARY OF THE INVENTION

The instant invention features radiolabeled fatty acids which exhibit high uptake and retention in the myocardium. In preferred embodiments the radiolabel is selected from the group consisting of $^{99m}$Tc, Re, $^{68}$Ga, $^{67}$Ga and $^{111}$In. The instant claimed fatty acid analogs are designed to be transported into myocardial cells by the same long chain fatty acid carrier protein mechanism as natural fatty acids. In addition, the agents provide stable chelation of the metal and cannot be completely catabolized in vivo. In this manner, transport/delivery and metabolism can be imaged after the tracer is retained intracellularly. Particularly preferred imaging agents show a heart-to-lung ratio of at least 2:1 within 30 minutes of administration.

The transport mechanism of the molecules described herein is a function of lipophilicity and neutrality derived from the fatty acid structure and the metal complex, respectively. Variation of the 1,2-dithio-5,8-diazacyclodecan moiety position within the fatty acid chain results in molecules that mimic fatty acids with respect to transport, and consequently, with reduced lung uptake. Separation of stereoisomers also improves the myocardial uptake and kinetics. Particularly preferred stereoisomers (R or S) are substanially pure (e.g. greater than about 75% isomeric purity).

The instant claimed labeled fatty acid can be used alone or in conjunction with myocardial flow agents. Other features and advantages of the instant invention will be apparent from the following Detailed Description and Claims.

DETAILED DESCRIPTION OF THE INVENTION

Imaging Agents and Methods for Making the Same

The instant claimed myocardial imaging agents have been designed, so that the termini of the fatty acid molecule is available or free of bonding and thus retains the transport and biochemical properties of the molecule. In addition, after being labeled with a suitable metal, the metal-chelate complex results in a neutral species, which therefore does not interfere with fatty acid transport to the heart tissue.

Two different routes have been used to develop radiolabeled fatty acids that do not drastically alter the predictable biological behavior of the carrier fatty acid. The first approach directly incorporates the radionuclide and chelating moiety into the very structure of the bio-molecule. Although this approach requires more skill on the design level, it preserves the size, shape, and structure of the driving bio-molecule. The key to this technique is in keeping the size of the metal and chelator as small as possible, thereby maintaining the natural properties and biodistribution of the bio-molecule.

In the second approach, the radionuclide is conjugated to the bio-molecule via a pendant chain. In this case, the radionuclide gets "carried" to the area of interest by the intact bio-molecule which has a known affinity for the target. Some advantages of this design include the unaltered active sites of the bio-molecule, the ability to change the length and location of the pendant chain, and the versatility of the chelating moiety at the end of the pendant chain.

The feasibility of attaching a pendant chain to the fatty acid is based on studies where fatty acids branched at position 3, 5 and 9 with Te-123m moieties were shown to have myocardial uptake equal to or higher than straight chain fatty acid [Elmaleh et al. 1981]. In addition, branching of one of the odd carbons of the fatty acid molecule will leave the termini of fatty acid molecule free. A metal-chelating group branched at these positions may allow the molecule to retain its fimdamental properties, for example avoiding β-oxidation.

A preferred metal chelating moiety is $N_2S_2$ bisaminothiol system along with the "3+1" chemistry involved in thiol conjugation. The "3+1" chemistry refers to fatty acids, which are assembled around the chelating moiety as described below, with the two separate ligands using 3 coordinating groups on one and one coordinating group on the other. Both systems allow for predictability and stable sequestration of the metal. The added advantage of the $N_2S_2$ chelator is that it exists as one geometric isomer which has been proven effective for chelation [Kung et al. 1997]. The "3+1" chelator system has advantages of versatility and derivatization. By applying both schools of thought, integration and conjugation, to both distinct chelating moieties, fatty acids are labeled with minimal effect on the biodistribution of the fatty acid.

The optimization of the relationship between various chelating groups and chain lengths may require the use of alkyl chains shorter or longer than C16 or C18, which are optimal in the case of straight and branched chain fatty acids.

To provide lipophilicity the alkyl chain should be 5 or more carbons. This optimal number was ascertained in the study of the hetero-atom Te in the Te fatty acid series [Elmaleh et al. 1981]. In addition, when labeled with the metal, the charge of the metal chelate moiety on the molecule must be neutral to facilitate initial membrane translocation into the heart tissue. Neither the older derivatives (Livni et al., 1979, Eckelman et al., 1975) nor the newer reported ones (Jones et al., 1990, Kelso et al., 1988, Mach et al., 1986, Davison et al., 1985) have possessed these properties.

The characterization of the metabolic fate of the claimed analogs can be accomplished by analysis of heart, blood and liver tissue at various times following administration of the labeled fatty acids to rats. A comparison of heart uptake characteristics of the labeled fatty acid analogs with those of [I-123]-(15-p-iodophenyl)-methylpentadecanoic acid (I-BMPPA) can then be performed.

R or S stereoisomers of the imaging agents may be purified from racemic mixtures as described in WO 97/19705 to Elmaleh, the teachings of which are incorporated herein by reference.

The following schemes generate labeled fatty acids that closely mimic the carrier fatty acid and therefore are stabile, predictable and neutral. Scheme 1 utilizes the well established $N_2S_2$ system to provide a robust, neutral metal(V)-oxo core.

Whereas in the past [Jones et al. 1994] the $N_2S_2$ fatty acid derivatives were prepared without regard to charge potential, the $N_2S_2$ chelator in the instant claimed compounds have been designed to possess a formal 3- charge. Therefore, upon addition of the metal-oxo (3+) core, the overall charge remains predictably neutral. Use of the neutral diaminodithiol analogs, of the type shown in Scheme 1, has a number of advantages: a) the acid and alkyl moieties are free and remote from the metal chelation site, b) the product is neutral and is expected to retain the general properties of a fatty acid, c) derivatives of diaminodithiol have proven to be good ligands for chelating metals, such as Tc-99m at room temperature with high radiochemical yield and radiochemical purity, d) the ligand core keeps the metal in a favored +5 oxidation state, and finally e) according to Davison and Jones, the size of the Tc-99m-diaminodithio chelate is similar to that of the phenyl group [Warren et al. 1986], which should not perturb the system. Another advantage of using this chelating strategy is that the $N_2S_2$ position on the molecule can be altered in order to determine its optimal location.

The structural modifications proposed for the instant described fatty acid derivatives will allow the compounds to retain their fundamental properties. The two series of $N_2S_2$-metal-fatty acids are shown in Scheme 1. In B one of the nitrogen donors, along with an ethylene bridge of the $N_2S_2$ chelating moiety, are part of the fatty acid chain, therefore keeping the molecular weight similar to that of the original physiological analog. The number of stereogenic centers created in B, produces a mixture of two erythro forms which can be separated by HPLC. Structure C provides an alternative route to a $N_2S_2$-Tc-labeled fatty acid. In this case the $N_2S_2$ chelating moiety is pendant to the fatty acid chain simplifying the stereo-chemical complexity involved with the chain of structure B.

Scheme 1

Series A  3 + 1 Chelation  "integration"

(1)

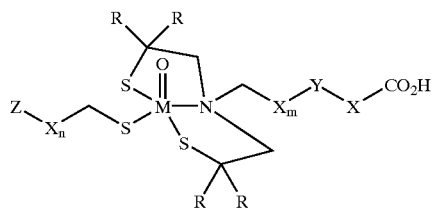

R = H or $CH_3$
n + m is in the range of 0 to 15, preferably 3 to 11
X = —$CH_2$— or —CH=
Y = —CH(R)— or —C(R)=
Z = $CH_3$— or $CH_2$=
M = metal, e.g., Re, Tc (2)

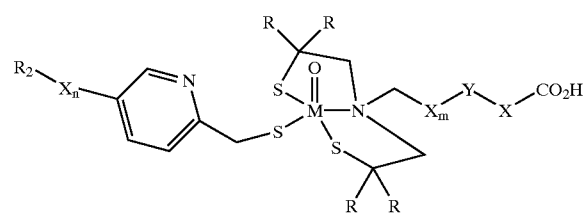

R = H or $CH_3$
n + m is in the range of 0 to 14, preferably 3 to 7 or 5 to 9
X = —$CH_2$— or —CH=
Y = —CH(R)— or —C(R)=
$R_2$ = H if n = 0, $CH_3$ if n > 1, or H or $CH_3$ if n = 1
M = metal, e.g., Re, Tc Series B  $N_2S_2$ Chelation "integration"

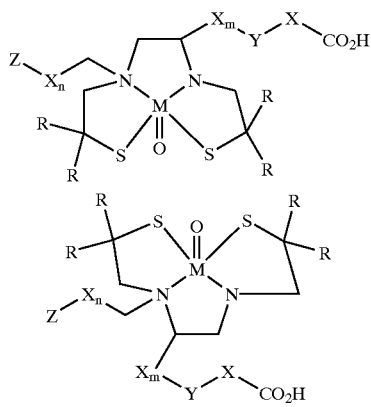

n + m is in the range of 8 to 17, preferably 9 to 14
X, Y, Z, and M are as defined above Series C  Chelation "pendant conjugation"

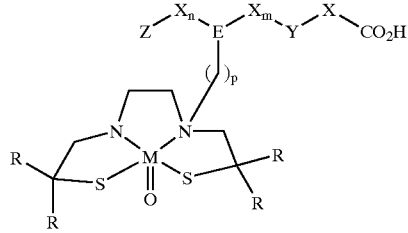

-continued

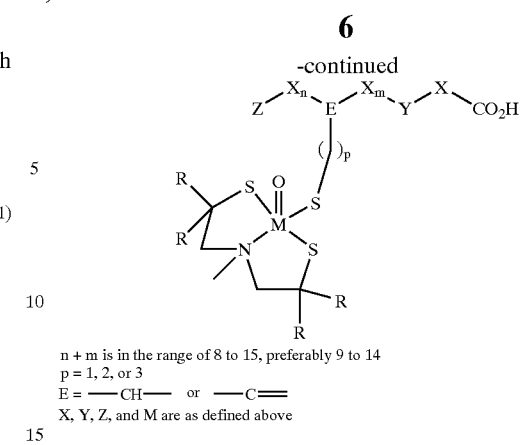

n + m is in the range of 8 to 15, preferably 9 to 14
p = 1, 2, or 3
E = —CH— or —C=
X, Y, Z, and M are as defined above Employing the 3+1 chemistry preserves the metal-oxo core, keeps the metal center in the favorable +5 oxidation state, and allows for easy derivation of both the donor atoms and R-groups of the tridentate, as well as monodentate ligands as illustrated in Scheme 2. In addition, by applying the versatile "3+1" system, the lipophilicity, size and donor groups can be "fine-tuned" to achieve the optimal biodistribution.

Scheme 2

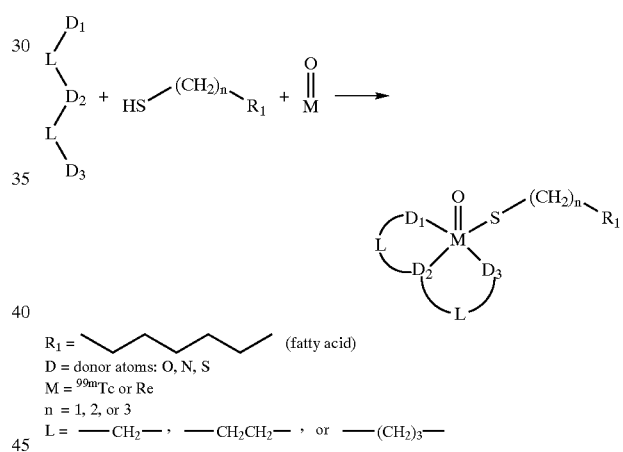

$R_1$ = ～～～～ (fatty acid)
D = donor atoms: O, N, S
M = $^{99m}Tc$ or Re
n = 1, 2, or 3
L = —$CH_2$—, —$CH_2CH_2$—, or —$(CH_2)_3$—

Once again the "3+1" chelation can facilitate either integration or pendant conjugation of the metal center. The "3+1" integration technique involves the joining of two distinct fragments of the fatty acid chain with the metal center positioned in the middle, as depicted in Scheme 1, series A. This technique allows for the obvious variations in the donor atoms, position of the metal center in the chain, and the interchanging of the "3" or "1" donor portions correlating to either the acid or carbon chain containing fragments of the fatty acid. Specifically, one fragment will be modified with a pendant thiol possessing a 1- charge, while the opposite fragment will be derivatized to possess three donor atoms with a 2- charge. The fragments will combine around the M=O center forming the neutral, chelated metal-fatty acid complex. While one fragment will be derivatized to possess a thiol group, the other fragment containing the "3" donors can be derivatized with any of the tridentate ligands shown in Scheme 3.

Scheme 3

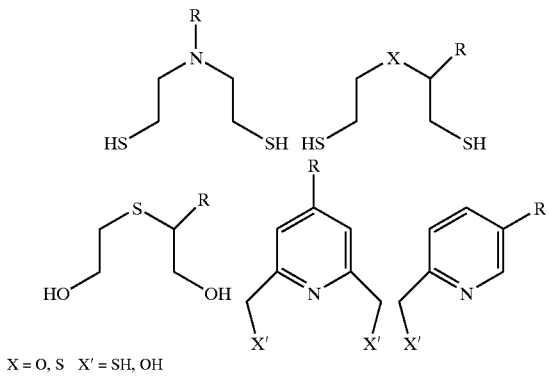

X = O, S  X' = SH, OH

Scheme 4

DADT  MAMA

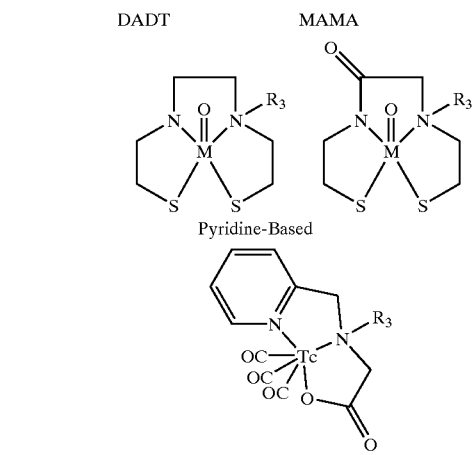

Pyridine-Based n + m is in the range of 7 to
16, preferably 8 to 15
X = —CH$_2$— or —CH=
Y = —CH(R)— or —C(R)=
Z = CH$_3$— or CH$_2$=
E = —CH— or —C=
M = metal, e.g., Re, Tc
p = 1, 2, or 3
R$_3$ =

The above, scheme 4 shows the DADT and MAMA N$_2$S$_2$ systems, as well as a pyrimidine based system. The pyridine-based chelating system takes advantage of the organometallic Tc(I) carbonyl chemistry recently developed. (Alberto et al., J. Am. Chem. Soc. (1998), 120: 7987–7988; Alberto et al., Transition Met. Chem. (1997) 22: 597–601) The chemistry of [$^{99m}$Tc(OH$_2$)$_3$(CO)$_3$]$^+$ has been elucidated and simplified to the point where the methods are routine and offer a practical alternative to the currently employed Tc(V) chemistry. In contrast to the highly reactive Tc(V)-oxo cores, where the chemistry is sometimes unpredictable, with necessary labeling clean-up steps, the Tc(I) method offers a distinct labeling alternative. The non-polar precursor Tc(CO)$_3$$^+$, with three tightly bound "innocent" carbonyls, provides three open coordination sites, allowing for a large degree of flexibility in the choice of ligands. Recent work has demonstrated the high affinity of the Tc(CO)$_3$$^+$ core for nitrogen donors. (Alberto et al., Transition Met. Chem. (1997) 22: 597–601; Leirer et al., Inorg. Chem. Acta (1999) 288: 150–153) The pendant pyridine molecule will provide just the right flexibility in atom donors to provide a stable Tc(I)-fatty acid complex.

In the past, organometallic Tc(I) complexes were extremely difficult to prepare and manipulate, requiring high temperatures and pressures. Today, [$^{99m}$Tc(OH$_2$)$_3$(CO)$_3$]$^+$ can be readily prepared in saline under 1 atm of carbon monoxide (CO). This water- and air-stable Tc(I) complex turns out to be a practical precursor to the formation of highly inert Tc(I) complexes, due in part to the formation of the d6 electron configuration of the metal center. The preparation of the organometallic aqua-ion is simple and straightforward, allowigng for convenient manipulation and product formation. The easy substitution of the labile H$_2$O ligands has been demonstrated, leaving the Tc(CO)$_3$$^+$ core intact. This stable core has the additional advantage of being smaller and less polar than the routinely employed Tc(V)-oxo systems. This could be a big advantage in biologically relevant systems where the addition of the metal center affects the size, shape, and potentially the bioactivity of the compounds.

Metal isotopes that can comprise the claimed structures include gallium and indium (e.g. $^{68}$Ga, $^{67}$Ga, $^{111}$In) in addition to technetium and rhenium. The properties of the Group VII metals technetium and rhenium are very similar due to their periodic relationship. It is anticipated that the metals will demonstrate similar reaction chemistry, which is often the case for the thiol, nitrogen, and oxo-chemistry of these two metals. Likewise, perrhenate and pertechnetate have very similar reaction behaviors. The similar reductions of the M(VII) oxo species by SnCl$_2$ allow for easy substitution of the nonradioactive rhenium as a model for the medicinally useful technetium-99m, which routinely uses tin reduced $^{99m}$Tc.

The "3+1" rhenium complexes are prepared by reacting [n-(C$_4$H$_9$)$_4$N]{ReOBr$_4$(OPPh$_3$)} [Cotton et al. 1966] with the tridentate thiol forming the [ReOX(S-Y-S)] intermediate, where X=Br or Cl and Y=N,S, or O [Fietz et al. 1995, Maresca et al. 1999]. The choice of [n-(C$_4$H$_9$)$_4$N]{ReOBr$_4$(OPPh$_3$)} as starting material was predicated on its potential clinical applications, ease of use, origination from ReCO$_4$—, and the finding that the more commonly employed oxorhenium(V)-halide starting material ReOCl$_4$— was extremely moisture sensitive [Zubieta et al. 1996]. The halide substitution by the monothiolated fatty acid is the final step in the metal thiolate formation as depicted in Scheme 2. The synthesis can also be performed in a "one-step" procedure with carefully added stoichiometric amounts of both the monothiol and tridentate ligands. Likewise, the N$_2$S2 rhenium complexes are easily prepared from both rhenium starting materials [n-(C$_4$H$_9$)$_4$N]{ReOBr$_4$(OPPh$_3$)} and [ReOCl$_3$(PPh$_3$)$_2$]. Rhenium reacts at room temperature with the addition of triethylamine as the base in relatively high yields. [Kung et al. 1997].

Vertebrate animals can be used to investigate the biodistribution and pharmacokinetics of new metal labeled fatty acids compounds to determine their ability to accurately measure uptake in the heart. For example, rats (Sprague Dawley, male, 150 at 80–100 grams each) can be used for the whole body biodistribution studies. Compounds can be evaluated with six time points 5, 10,15, 30, 60, and 120 minutes with five animals per time point, so that accurate statistics in the clearance rate measurements can be obtained, accounting for intraspecies variation.

Pharmaceutical Compositions and Use

The imaging agents of the invention may be prepared as pharmaceuticals and an effective amount (e.g. from about 1 to about 50 mCi, more preferably between 10–30 mCi) administered to a subject to identify cardiac dysfunction, including cardiac ischemia, cardiomyopathy, tissue viability, hybrinating heart and other cardiac abnormalities Compositions for use in accordance with the present invention may be formulated in a conventional manner using one or more physiologically acceptable carriers or excipients. Thus, the compounds and their physiologically acceptable salts and solvates may be formulated for administration by, for example, injection or parenteral administration.

The compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives, In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In another embodiment, the invention provides a kit for imaging, which comprises one or more of the imaging agents described above, in combination with a pharmaceutically acceptable solution containg a carrier such as human serum albumin or an auxiliary molecule, such as mannitol or gluconate. The kits of the invention may include additional components, which facilitate practice of the method of the invention, including buffers, syringes, film, instructions, and the like.

The contents of all cited references (including literature references, issued patents, published patent applications as cited throughout this application) are hereby expressly incorporated by reference. The practice of the present invention will employ, unless otherwise indicated, conventional techniques that are within the skill of the art. Such techniques are explained fully in the literature.

References

Alberrto, R., et al., (1998) *J. Am. Chem. Soc.* 120: 7987–7988.

Alberto, R., et al., (1997) *Transition Met. Chem* 22: 597–601.

Alberto, R., et al., (1999) *J. Am. Chem. Soc.* 121: 6076–6077.

Bassingthwaighte J B, Halloway G A: Estimation of blood flow with radioactive tracers. Semin. Nucl. Med. 6 141–161, 1976.

Bianco J A, Pape L A, Alpert J S, Zheng M, Hnatowich D, Goodman M M, Knapp F F: Accumulation of radioiodinated 15-(p-iodophenyl)-6-tellurapentadecanoic acid in ischemic myocardium during acute coronary occlusion and reperfusion. J. Am. Coll. Cardiol. 4:80–87, 1984.

Corbin, J L, Work D E: 1-alkyl- (or aryl-) amino-2-methylpropane-2-thiols. Some bi- and tetradentate nitrogen-sulfur ligands from Schiff s base disulfides. J. Org. Chem. 41: 489–491, 1976.

Davison A, Jones A G, Lister-James J, et al: Fatty acid derivatives -substituted with a neutral technetium complex. J. Nucl. Med. 26: P4, 1985 (abstr.).

Davison A, Jones A G: Private Communication.

Davison A, Jones A G, Orvig C, et al: A new class of oxotechnetium (5+) chelate complexes containing a $TcON_2S_2$ core. Inorg. Chem. 20: 1629–1631, 1981.

Dudczak R, Kletter K, Frischauf H, et al: The use of $^{123}$I-labeled heptadecanoic acid (HAD) as metabolic tracer: Preliminary report, Eur. J. Med. 9: 81–85, 1984.

Eckelman W C, Karesh S M, Reba R C: New compounds: Fatty acid and long chain hydrocarbon derivatives containing a strong chelating group. J. Pharm. Sci. 64: 704–706, 1975

Elmaleh D R, Knapp F F Jr, Yasuda T, et al: Myocardial imaging with 9-(Te-123m) telluraheptadecanoic acid. J. Nucl. Med. 22: 994–999, 1981.

Gately S J, Halama J R, Holden J E, et al: On the rate-limiting step in myocardial clearance of label from 16-iodohexadecanoic acid. J. Nucl. Med. 24: P12, 1983 (abstr.).

Goldfarb H W, Scheffel U, Lever S Z, et al: Comparison of Tc-99m aminoethyl diaminodithiol analogs for brain blood flow imaging. J. Nucl. Med. 27:1050, 1986 (abstr.).

Goldstein R A, Klein M S, Welch M J, et al: External assessment of myocardial metabolism with C-1 lpalmitate in vivo. J. Nucl. Med. 21: 342–348, 1980.

Goodman, M M, Kirsch G, Knapp F F, Jr: Synthesis and evaluation of radioiodinated terminal p-iodophenyl-substituted αα- and ββ-methyl branched fatty acids. J. Med. Chem. 27: 390–397, 1984

Goodman M M, Knapp F F Jr., Elmaleh D R, et al: New Myocardial imaging agents. Synthesis of 15-(p-iodophenyl)-3(R,S) methylpentadecanoic acid by decomposition of a 3,3-(1,5-pentanedyl) triazene precursor. J. Org. Chem. 49: 2322–2325, 1984.

Heymann M A, Payne B D, Hoffinan J E, Rudolph A M: Blood flow measurements with radionuclide-labeled particles. Prog. Cardiovasc. Dis. 20: 55–79, 1977.

Kung H F, Guo Y-Z, Mach R H, et al: New Tc-99 complexes based on $N_2S_2$ ligands. J. Nucl. Med. 27 1051, 1986 (abstr.).

Kung H F, Molnar M, Billings J, et al: Synthesis and biodistribution of neutral lipid-soluble Tc-99m complexes that cross the blood-brain barrier. J. Nucl. Med. 25: 326–332, 1984.

Kung H F, Yu C C, Billings J, et al: Synthesis of new bis(aminoethanethiol) (BAT) derivatives: Possible ligands for $^{99m}$Tc brain imaging agents. J. Med. Chem. 28 1280–1284, 1985.

Leirer, M. et al., (1999) Inorg. Chim. Acta 288: 150–153.

Lerch R A, Bergmann S R, Ambos H D, et al: Effect of flow independent reduction of metabolism on regional myocardial clearance of $^{11}$c-palmitate. Circulation 65: 731–738, 1982.

Lever S Z, Bums H D, Kervitsky T M, et al: Design, preparation and biodistribution of a technetium-99m triaminedithiol complex to assess regional cerebral blood flow. J. Nucl. Med. 26: 1287–1294, 1985

Liefhold J, Eisenhut M: Synthesis, labeling and pharmacokinetics of 131 I labeled phenylene-iodophenyl fatty acids (PHIPA): *Proceedings 6$^{th}$ Int. Symp. Radiopharm. Chem.*, Boston, 1986, pp 212–214 (abstr.).

Livni E, Davis M A, Warner V D: Synthesis and biological distribution of Tc-99m labeled palmitic acid derivatives. *In Radiopharmaceuticals II. Proceeding 2$^{nd}$ Int. Smp. Radiopharmaceuticals.* New York, Society of Nuclear Medicine, 1979, pp. 265–274.

Livni E, Elmaleh D R, Barlai-Kovach M M, et al: Radioiodinated betamethyl phenyl fatty acids as tracers for myocardial imaging and metabolism. Eur. Heart J. (Suppl B), 6: 85–89, 1985.

Livni E, Elmaleh D R, Levy S, et al: Beta-methyl (1-$^{11}$C) heptadecanoic acid: Ac new myocardial metabolic tracer for positron emission tomography. J. Nuel. Med. 23: 169–175, 1982.

Mach R H, Kung H F, Xu X-J, et al: Synthesis and biodistribution of Tc-99m BAT-PDA: A potential imaging agent for SPECT. *Proceedings 6$^{th}$ Int. Syp. Radiopharm. Chem.* Boston, 1986, pp. 110–112 (abstr.).

Machulla H J, Stocklin G, Kupfemagel C, et al; Comparative evaluation of fatty acids labeled with C-11, Cl-34m, Br-77 and I-123 for metabolic studies of the myocardium. Concise Communication. J. Nucl. Med. 19:298–302, 1978.

Miller D D, Barlai-Kovach M M, Gill J B, Livni E., Elmaleh DR, et al: Imaging characteristics of a new single photon myocardial metabolic tracer. Circulation, 74, Suppl. II, 245 (1986).

Miller D D, Gill J B, Barlai-Kovach M, et al: Modified fatty acid analog imaging: Correlation of SPECT and clearance kinetics in ischemic-reperfused myocardium. J. Nucl. Med. 26; p88, 1985 (abstr.).

Most A S, Brachfeld N, Gorlin R, et al: Free fatty acid metabolism of the human heart at rest. J. Clin. Invest. 48:1177, 1969.

Neely J R, Morgan H E: Relationship between carbohydrate and lipid metabolism and the energy balance of heart muscle. Ann. Rev. Physiol. 36: 413–459, 1974.

Neely, J R, Rovetto M J, Gram J F: Myocardial utilization of carbohydrates and lipids. Progr. Cardiovasc. Res. 15:289, 1972.

Nelson G J: Isolation and purification of lipids from animal tissue. In Analysis of Lipids and Lipoproteins, Perkins, E G., E d. American Oil Chemist's Society, Champaign IL., 1975, pp. 1–22.

Opie L M: Metabolism of the heart in health and disease. Am. Heart J. 76: 685, 1968

Poe N D, Robinson G D Jr., MacDonald N S: Myocardial extraction of labeled long-chain fatty acid analogs. Proc. Soc. Exp. Biol. Med 148:215, 1975.

Reske S N, Sauer W, Machulla H J, et al: 15-(p-($^{123}$I) iodophenyl)- pentadecanoic acid as tracer of lipid metabolism: Comparison with (1-$^{14}$C) palmitic acid in murine tissues. J. Nucl. Med. 25: 1335–1342, 1984.

Rovett M J: Cardiac metabolism. In: Cardiac Pharmacology. Academic Press, New York, 1981, pp. 335–359.

Schelbert H R: Radionuclide assessment of myocardial metabolism. In: Freeman L M, Johnson P. (eds) Clinical Radionuclide Imaging, vol. 1. Grune & Stratton, New York, 1984, pp. 563–558.

Schelbert H R: The emergence of positron emission tomography as a clinical tool for studying local myocardial function. In: Freeman L M, Weissman H S, (ads) Nuclear Medicine Annual Raven Press. New York, 1984, pp. 141–161.

Schelbert H R, Henze E, Schon H R, Keen R, Hansen H, Selin C, Huang S C, Barnio J R, Phelps M E: C-I palmitate for the noninvasive evaluation of regional myocardial fatty acid metabolism with pogitron computed tomography. III. In vivo demonstration of the effects of substrate availability on myocardial metabolism. Am. Heart J. 105: 492–504, 1983.

Schon H R, Senekowitsch R, Berg D, et al: Measurement of myocardial fatty acid metabolism: Kinetics of iodine-123 heptadecanoic acid in normal dog heart. J. Nucl. Med. 27: 1449–1455, 1986.

Schon H R, Schelbert H R, Robinson G, et al: C-11 palmitic acid for the noninvasive evaluation of regional fatty acid metabolism with positron-computed tomography. Am. Heart J. 103: 532–561, 1982.

Sobel B E, Weiss E S, Welch M J, et al: Detection of remote myocardial infarction in patients with positron emission transaxial tomography and intravenous $^{11}$C-palmitate. Circulation, 55: 851–853,1977.

Van der Wall E E, Westera G, Heidendal GAK.: A comparison between terminally radioiodinated hexadecanoic acid and heptadecanoic acid in the dog heart. Eur. J. Med. 6: 581–584, 1981.

Warren G L, Caldwell J H, Kremer P A, et al: New iodinated phenyl fatty acids for imaging myocardial metabolism. J. Nucl. Med. 27: 939–940, 1986 (abstr.).

Watson A D, Walaovitch R C, Belonga B O, et al: The chemistry and pharmacology of triaminedithiol technetium-based perfusion agents. *Proceedings 6$^{th}$ Int. Symp. Radiopharm. Chem.*, Boston, 1986, pp.E122–123 (abstr.).

Weich H F, Strauss H W, Pitt B: The extraction of thallium-201 by the myocardium. Circulation 56: 188–191, 1977.

Weiss E S, Hoffnan E J, Phelps M E, et al: External detection and visualization of myocardial ischemia with $^{11}$C-substrates in vitro and in vivo. Circ. Res. 39: 24–32, 1976

Westera G, van der Wall E E, Heidendal GAK, et al: A comparison between terminally radioiodinated hexadecenoic acid (I-HA) and T1–201-thallium in the dog heart. Implications for the use of I-HA for myocardial imaging. Eur. J. Nucl. Med. 5: 339–343, 1980.

Whitmer T T, Idell-Wenger J A, Rovetts M J, et al: Control of fatty acid metabolism in ischemia and hypoxic heart. J. Biol. Chem. 253: 4305–4309, 1978.

Zieler K L: Fatty acids as substrates for heart and skeletal muscles. Circ. Res. 38: 459–463, 1976.

Bandoli G, Mazzi U, Pietzsch H-J, Spies H. Acta. Crystallogr. Sect C. 48: 1422, 1992.

Clarke M J, Podbielski L., Medical diagnostic imaging with complexes of $^{99m}$Tc. Coord. Chem. Rev. 78: 253–331, 1987.

Fietz T, Spies H, Pietzsch H-J, Leibnitz. Inorg. Chim. Acta 231: 233, 1995.

Hom R K, Katzenellenbogen J A. Technetium-99m-labeled receptor-specific small-molecule radiopharmaceuticals: recent developments and encouraging results. Nuc. Med. and Biol. 24: 485–498, 1997.

Johannsen B, Scheunemann M, Spies H, Brust P, Wober J, Syhre R, Pietzsch H-J. Technetium (V) and rhenium (V) complexes for 5-HT2A serotonin receptor binding: structure-affinity considerations. Nuc. Med. and Biol. 23: 429–438, 1996.

Maresca K P, Femia F J, Babich J W, Zubieta J. Expansion of the '3+1' concept of oxorhenium-thiolate chemistry to cationic and binuclear complexes. Inorg. Chem. Comm. 1: 209–212, 1998.

Maresca K P, Bonavia G H, Babich J W, Zubieta J. Synthesis and characterization of oxorhenium '3+1' mixed-thiolate complexes. Inorg. Chim. Acta 284: 252–257, 1997.

Meegalla S K, Plossl K, Kung M P, Chumpradit S, Stevenson A D, Kushner S A, McElgin W T, Mozley D P, Kung H F. Synthesis and characterization of Tc-99m-labeled tropanes as dopamine transporter-imaging agents. J. Med. Chem. 40: 9–17, 1997.

Nicholson T, Cook J, Davison A, Rose D J, Maresca K P, Zubieta J A, Jones A G. The synthesis and characterization of [MCl₃(N=NC₅H₄NH)(HN=NC₅H₄N)] from [MO₄]⁻ (where M=Re, Tc) organodiazenido, organodiazene-chelate complexes." Inorg. Chim. Acta 252: 421–426, 1996.

Rose D J, Maresca K P, Nicholson T, Davison A, Jones A G, Babich J W, Fischman A, Graham W, DeBord JRD, Zubieta J. Synthesis and characterization of organohydrazino complexes of technetium, rhenium, and molybdenum with the {M(η1-HxNNR)(η2-HyNNR)} core and their relationship to radiolabeled organohydrazine derivatized chemotactic peptides with diagnostic applications. Inorg. Chem. 37: 2701–2716, 1998.

Rose D J, Maresca K P, Kettler P B, Chang Y D, Soghomonian V, Chen Q, Abrams M J, Larsen S K, Zubieta J. Synthesis and characterization of rhenium thiolate complexes." Inoganic Chemistry 35: 3556, 1995.

What is claimed is:

1. A fatty acid analog, wherein the analog has the formula:

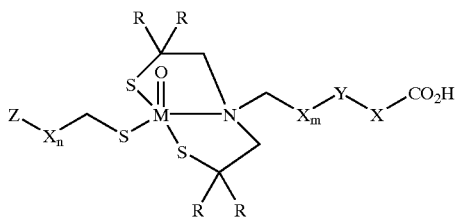

wherein R represents H or Me,

X represents —CH$_2$— or —CH═,

Y represents —CH(R)— or —C(R)═,

Z represents CH$_3$— or CH$_2$═,

M represents a radioisotope, and the sum of m+n is in the range of 0 to 15.

2. The fatty acid analog of claim 1, wherein the sum of m+n is in the range of 3 to 11.

3. A fatty acid analog, wherein the analog has the formula:

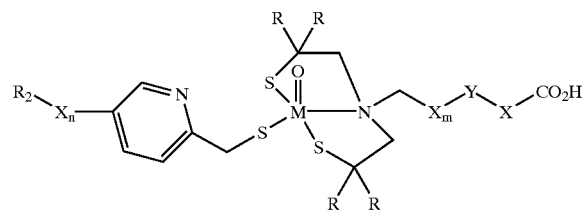

wherein R represents H or Me,

X represents —CH$_2$— or —CH═,

Y represents —CH(R)— or —C(R)═,

M represents a radioisotope, and the sum of m+n is in the range of 0 to 14.

4. The fatty acid analog of claim 3, wherein the sum of m+n is in the range of 3 to 7.

5. The fatty acid analog of claim 3, wherein the sum of m+n is in the range of 5 to 9.

6. A fatty acid analog, wherein the analog has the formula:

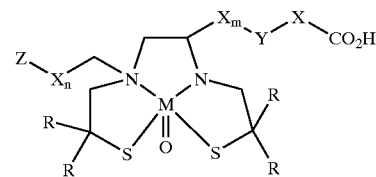

wherein R represents H or Me,

X represents —CH$_2$— or —CH═,

Y represents —CH(R)— or —C(R)═,

Z represents CH$_3$— or CH$_2$═,

M represents a radioisotope, and the sum of m+n is in the range of 8 to 17.

7. The fatty acid analog of claim 6, wherein the sum of m+n is in the range of 9 to 14.

8. A fatty acid analog, wherein the analog has the formula:

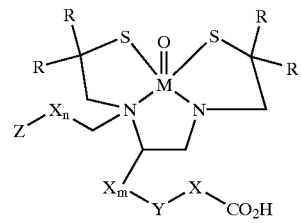

wherein R represents H or Me,

X represents —CH$_2$— or —CH═,

Y represents —CH(R)— or —C(R)═,

Z represents CH$_3$— or CH$_2$═,

M represents a radioisotope, and the sum of m+n is in the range of 8 to 17.

9. The fatty acid analog of claim 8, wherein the sum of m+n is in the range of 9 to 14.

10. A fatty acid analog, wherein the analog has the formula:

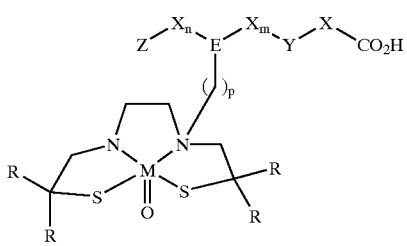

wherein R represents H or Me,
X represents —$CH_2$— or —CH=,
Y represents —CH(R)— or —C(R)=,
Z represents $CH_3$— or $CH_2$=,
E represents —CH— or —C=,
M represents a radioisotope,
p represents 1, 2, or 3,
and the sum of m+n is in the range of 8 to 17.

11. The fatty acid analog of claim 10, wherein the sum of m+n is in the range of 9 to 14.

12. A fatty acid analog, wherein the analog has the formula:

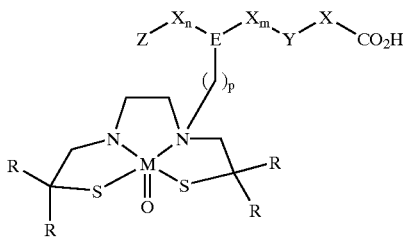

wherein R represents H or Me,
X represents —$CH_2$— or —CH=,
Y represents —CH(R)— or —C(R)=,
Z represents $CH_3$— or $CH_2$=,
E represents —CH— or —C=,
M represents a radioisotope,
p represents 1, 2, or 3,
and the sum of m+n is in the range of 8 to 17.

13. The fatty acid analog of claim 12, wherein the sum of m+n is in the range of 9 to 14.

14. A fatty acid analog comprising at least one ligand complexed to a radioisotope, wherein the radioisotope has a neutral charge, the analog comprises an alkyl terminus and a carboxylic acid terminus, and the carboxylic acid is remote from the radioisotope, wherein the radioisotope complex comprises one ligand with three donor atoms complexed to the radioisotope and one ligand with one donor atom complexed to the radioisotope.

15. A fatty acid analog, wherein the analog has the formula:

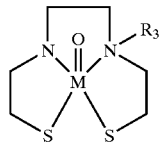

wherein $R_3$ represents:

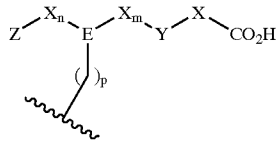

X represents —$CH_2$— or —CH=,
Y represents —CH(R)— or —C(R)=,
Z represents $CH_3$— or $CH_2$=,
E represents —CH— or —C=,
M represents a radioisotope,
and the sum of m+n is in the range of 7 to 16.

16. The fatty acid analog of claim 15, wherein the sum of m+n is in the range of 8 to 15.

17. A fatty acid analog, wherein the analog has the formula;

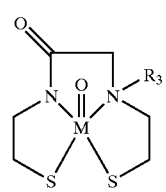

wherein $R_3$ represents

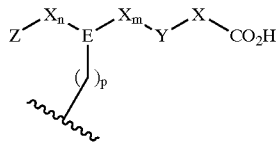

X represents —$CH_2$— or —CH=,
Y represents —CH(R)— or —C(R)=,
Z represents $CH_3$— or $CH_2$=,
E represents —CH— or —C=,
M represents a radioisotope,
and the sum of m+n is in the range of 7 to 16.

18. The fatty acid analog of claim 17, wherein the sum of m+n is in the range of 8 to 15.

19. A fatty acid analog, wherein the analog has the formula:

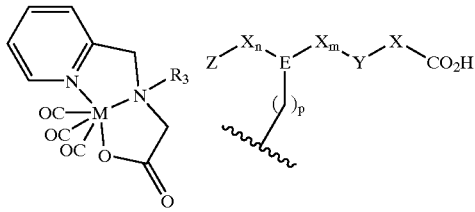

wherein $R_3$ represents
X represents —$CH_2$— or —CH=,
Y represents —CH(R)— or —C(R)=,
Z represents $CH_3$— or $CH_2$=, E represents —CH— or —C=, M represents a radioisotope, and the sum of m+n is in the range of 7 to 16.

20. The fatty acid analog of claim 19, wherein the sum of m+n is in the range of 8 to 15.

21. A fatty acid analog comprising at least one ligand complexed toa radioisotope, wherein the radioisotope has a neutral charge, the analog comprises an alkyl terminus and a carboxylic acid terminus, and the carboxylic acid is remote from the radioisotope, wherein the analog is chiral and is a substantially pure (S) diastereomer.

22. A fatty acid analog comprising at least one ligand complexed toa radioisotope, wherein the radioisotope has a neutral charge, the analog comprises an alkyl terminus and a carboxylic acid terminus, and the carboxylic acid is remote from the radioisotope, wherein the analog is chiral and is a substantially pure (R) diastereomer.

23. The fatty acid analog as in any of the preceding claims wherein the analog localizes to a heart in preference to a lung when administered to an organism.

24. The fatty acid analog as in any of the preceding claims wherein the radioisotope is selected from $^{99m}$TC, Re, $^{68}$Ga, $^{67}$Ga, and $^{111}$In.

* * * * *